United States Patent [19]

Watanabe et al.

[11] Patent Number: 5,508,244
[45] Date of Patent: Apr. 16, 1996

[54] PRETREATMENT PROCESS OF ZEOLITE CATALYST AND PROCESS FOR PRODUCING ALCOHOL USING THE PRETREATED CATALYST

[75] Inventors: Kouji Watanabe, Mizumaki; Yutaka Mori, Kitakyushu, both of Japan

[73] Assignee: Mitsubishi Chemical Corporation, Tokyo, Japan

[21] Appl. No.: 293,208

[22] Filed: Aug. 19, 1994

[30] Foreign Application Priority Data

Aug. 27, 1993 [JP] Japan .................... 5-212759

[51] Int. Cl.$^6$ ............................... B01J 29/06
[52] U.S. Cl. ............................... 502/64; 568/695
[58] Field of Search ................. 502/61, 63, 64; 568/695

[56] References Cited

U.S. PATENT DOCUMENTS

| | | |
|---|---|---|
| 4,326,994 | 4/1982 | Haag et al. . |
| 4,418,235 | 11/1983 | Haag et al. . |
| 4,588,846 | 5/1986 | Mitsui et al. . |
| 5,231,233 | 7/1993 | Le et al. ................. 502/64 X |
| 5,250,277 | 10/1993 | Kresge et al. ........... 208/46 X |

FOREIGN PATENT DOCUMENTS

| | | |
|---|---|---|
| 57-70828 | 5/1982 | Japan . |
| 58-124723 | 7/1983 | Japan . |
| 58-194828 | 11/1983 | Japan . |

*Primary Examiner*—Michael Lusignan
*Attorney, Agent, or Firm*—Oblon, Spivak, McClelland, Maier & Neustadt

[57] ABSTRACT

Disclosed are a pretreatment process of a zeolite as a catalyst for producing an alcohol by hydration of an olefin, comprising keeping the zeolite in contact with water before the hydration, and a process for producing an alcohol which comprises hydrating an olefin in the presence of a zeolite catalyst obtained by keeping a zeolite as a catalyst in contact with water.

12 Claims, No Drawings

PRETREATMENT PROCESS OF ZEOLITE CATALYST AND PROCESS FOR PRODUCING ALCOHOL USING THE PRETREATED CATALYST

BACKGROUND OF THE INVENTION

The present invention relates to a pretreatment process of a zeolite catalyst and a process for producing an alcohol using the pretreated zeolite catalyst. The pretreated zeolite catalyst is useful for the production of alcohols through hydration of olefins.

Hydration of olefins in a homogeneous system in the presence of a catalyst such as a mineral acid or the like has been generally employed for the industrial production of alcohols. In recent years, the alcohol production processes using a solid acid catalyst, especially a zeolite as catalyst for the hydration have been proposed in place of the conventional process (For example, Japanese Patent Application Laid-Open (KOKAI) Nos. 57-70828 (1982), 58-124723 (1983) and 58-194828 (1983)).

However, it is difficult to obtain a sufficient catalyst activity even by using a zeolite as catalyst, and in order to obtain a reaction rate well satisfactory for the industrial process, it is necessary to raise the reaction temperature. Hydration of olefins is usually exothermic, and the ratio of alcohol to olefin at equilibrium decreases with rise of temperature.

Therefore, rise of reaction temperature leads to a reduced concentration of alcohol as the product, and as a consequence, a great deal of cost is required for separation and recovery of olefin as the starting material and alcohol as the product. Further, rise of reaction temperature causes a corresponding elevation of not only the hydration rate of the olefin but also the rate of its conversion to the by-products through side reactions such as isomerization, which may result in a reduced selectivity of the hydration.

By the studies for overcoming the above problems, the present inventors have found that by using as a catalyst of hydration of an olefin, zeolite which has been kept in contact with water, the hydration can be proceed with remarkably high catalytic activity as compared with the conventional process. The present invention has been attained based on the finding.

SUMMARY OF THE INVENTION

An object of the present invention is to provide a pretreatment process of a zeolite as a catalyst for producing an alcohol from an olefin in a high yield.

Another object of the present invention is to provide a process for producing an alcohol from an olefin in a high yield.

In a first aspect of the present invention, there is provided a pretreatment process of a zeolite as a catalyst for producing an alcohol by hydration of an olefin, comprising keeping the zeolite in contact with water before the hydration.

In a second aspect of the present invention, there is provided a process for producing an alcohol which comprises hydrating an olefin in the presence of a zeolite catalyst obtained by keeping a zeolite as a catalyst in contact with water.

DETAILED DESCRIPTION OF THE INVENTION

Examples of the zeolites usable in the present invention include crystalline aluminosilicates such as mordenite, erionite, ferrierite and ZSM zeolites developed by Mobil Oil Corp.; aluminometallosilicates containing foreign elements such as boron, iron, gallium, titanium, copper, silver, etc.; and metallosilicates substantially free of aluminum, such as gallosilicates and borosilicates. As regards the cationic species which are exchangeable in the zeolites, the proton-exchanged type (H-type) zeolites are usually used, but it is also possible to use the zeolites which have been ion-exchanged with at least one cationic species, for example, an alkaline earth element such as Mg, Ca and Sr, a rare earth element such as La and Ce, a VIII-group element such as Fe, Co, Ni, Ru, Pd and Pt, or other element such as Ti, Zr, Hf, Cr, Mo, W and Th.

The present invention is characterized in that a zeolite such as mentioned above is kept in contact with water as a pretreatment. The zeolite to be treated refers to an already synthesized zeolite, that is, calcined zeolite, and such treatment does not include contact with water in the hydrothermal reaction or ion exchange in the synthesis process of the zeolite.

The amount of water to be contacted with zeolite may be properly selected provided that the selected amount is sufficient to effect desired contact between water and zeolite, but it is usually not less than 0.01 time by weight, preferably not less than 0.1 time by weight, more preferably 0.1 to 50 times by weight that of zeolite to be treated. The time period in which zeolite is kept in contact with water may be determined by taking various operational conditions into consideration, but for obtaining a satisfactory catalytic activity, the water-zeolite contact time is usually not less than one hour, preferably about 3 to 1,000 hours. The temperature at which zeolite is contacted with water may be properly selected from the industrially practicable range. Too low temperature may fail to provide the desired effect while too high temperature may cause disruption of the acid sites or structure of the zeolite, so that the contact temperature is usually 50 to 300° C., preferably 80 to 250° C.

As for means for keeping contact between zeolite and water, there may be employed either a method using water as a liquid phase or a method in which water is turned into vapor and used as a gaseous phase. The contact may be attained under normal pressure or under pressure, or if necessary, under reduced pressure. In case of using water as a liquid phase, zeolite is provided as a suspended or fixed bed. The treatment may be carried out either continuously or batchwise, with stirring if necessary.

The zeolite which has been subjected to the contact treatment with water may be recovered by separating it from water by suitable means such as filtration. It needn't be dried and may be directly used for the hydration. Also, water used for the contact treatment may not be separated, and the mixture may be subjected to the hydration by adding an olefin and, if necessary, additional water.

The olefin hydration can be performed by a known method using a zeolite as catalyst.

The olefins to be hydrated with a zeolite catalyst treated according to the present invention are preferably straight-chain or branched olefins or cyclic olefins having 2 to 12 carbon atoms. Examples of such olefins include ethylene, propylene, 1-butene, 2-butene, isobutene, pentenes, hexenes, heptenes, octenes, cyclobutene, cyclopentene, methylcyclopentenes, cyclohexene, methylcyclohexenes, cyclooctene, cyclododecene and the like. The zeolite catalysts of the present invention are especially effective for the hydration reaction of the cyclic olefins generally with a low hydration rate and a low equilibrium alcohol concentration.

Regarding the hydration conditions, the reaction temperature is usually 50° to 250° C. preferably 70° to 200° C. and the reaction pressure is preferably above a pressure necessary for maintaining the olefin in a liquid phase under the applied reaction conditions. The reaction pressure may be adjusted with an inert gas such as nitrogen gas. The amount of water used for the reaction is usually about 1 to 100 moles per mole of the olefin used. The reaction may be conducted in the presence of other organic solvent including alcohols, ketones, phenols and the like. The reaction form may be either batchwise or continuous, and any of the commonly used reaction methods such as stirring type, fixed bed type, fluidized bed type, etc., can be employed. The amount (weight ratio) of the catalyst used is usually about 0.01 to 200, preferably 0.1 to 20 based on the olefin, in the case of batchwise reaction. In the case of the continuous reaction, the olefin is supplied in a rate of usually 0.1 to 10 kg/hr per kilogram of catalyst, preferably 0.3 to 3 kg/hr per kilogram of catalyst, more preferably 0.5 to 2 kg/hr per kilogram of catalyst.

EXAMPLES

The present invention is further illustrated with reference to the examples thereof. However, the examples are merely intended to be illustrative and not to be construed as limiting the scope of the invention.

Example 1

300 g of an H-type crystalline aluminosilicate (produced by NE Chemcat Corp., silica/alumina=50/1) and 350 g of water were placed in a one-liter stainless steel-made pressure vessel. After the interior of the vessel was pressurized to 2 kg/cm$^2$G with nitrogen gas, the treatment was carried out at 180° C. for 12 hours, followed by a filtration.

Then 30 g of cyclohexene, 60 g of water and 20 g of the obtained zeolite were placed in a 200 cc autoclave having a stirrer, and after the interior of the autoclave has been pressurized to 2 kg/cm$^2$G with nitrogen gas, a cyclohexene hydration was carried out at 120° C. with stirring at 1,000 r.p.m. for one hour. The oil and aqueous phases of the reaction solution were analyzed by gas chromatography and the calculated cyclohexanol yield was 12.8%.

Comparative Example 1

A cyclohexene hydration was carried out by following the same procedure as Example 1 except that no pretreatment was conducted. The cyclohexanol yield was 10.8%.

Example 2

An H-type aluminoferrosilicate (MFI type, produced by NE Chemcat Corp., silica/(Fe$_2$O$_3$+alumina)=50/1, Fe$_2$O$_3$/alumina=1/1) was subjected to pretreatment in the same way as Example 1. A cyclohexene hydration was carried out by using this zeolite in the same way as Example 1, the cyclohexanol yield was 13.4%.

Comparative Example 2

A cyclohexene hydration was carried out by following the same procedure as Example 2 except that no pretreatment was conducted. The cyclohexanol yield was 10.5%.

Example 3

25 g of an H-type gallosilicate (MFI type, produced by NE Chemcat Corp., silica/Ga$_2$O$_3$ 32 50/1) and 40 g of water were placed in a 100 ml stainless steel-made pressure vessel, and after the interior of the vessel was pressurized to 2 kg/cm$^2$G with nitrogen gas, the treatment was carried out at 140° C. for 200 hours. A cyclohexene hydration was carried out by using this zeolite in the same way as Example 1, and the cyclohexanol yield was 11.4%.

Comparative Example 3

A cyclohexene hydration was carried out by following the procedure of Example 3 except that no pretreatment was conducted. The cyclohexanol yield was 10.0%.

Examples 4 to 7

In the process of Example 3, an H-type ZSM-5 (produced by NE Chemcat Corp., silica/alumina=50/1) was pretreated by changing the treating temperature and time. The cyclohexanol yields are shown in Table 1.

TABLE 1

| | Treating temp. (°C.) | Treating Time (hr) | Cyclohexanol yield (%) |
|---|---|---|---|
| Example 4 | 120 | 500 | 12.1 |
| Example 5 | 180 | 5 | 11.9 |
| Example 6 | 180 | 210 | 12.5 |
| Example 7 | 200 | 500 | 12.0 |

Examples 8 to 11

In the process of Example 3, an H-type aluminosilicate (MFI type, produced by NE Chemcat Corp.; silica/(Fe$_2$O$_3$+alumina)=50/1, Fe$_2$O$_3$/alumina=1/1) was pretreated by changing the treating temperature and time. The cyclohexanol yields are shown in Table 2.

TABLE 2

| | Treating temp. (°C.) | Treating Time (hr) | Cyclohexanol yield (%) |
|---|---|---|---|
| Example 8 | 120 | 500 | 12.5 |
| Example 9 | 180 | 5 | 11.5 |
| Example 10 | 180 | 210 | 12.7 |
| Example 11 | 200 | 500 | 11.6 |

Examples 12 and 13

In the process of Example 3, an H-type Ga-silicate (MFI type, produced by NE Chemcat Corp., silica/Ga$_2$O$_3$=50/1) was pretreated by changing the treating temperature and time. The cyclohexanol yields are shown in Table 3.

TABLE 3

| | Treating temp. (°C.) | Treating Time (hr) | Cyclohexanol yield (%) |
|---|---|---|---|
| Example 12 | 120 | 500 | 10.7 |
| Example 13 | 140 | 200 | 11.4 |

What is claimed is:

1. A pretreatment process of a zeolite as a catalyst for producing a cyclic alcohol by hydration of a cyclic olefin, comprising keeping the zeolite in contact with water before the hydration.

2. A pretreatment process according to claim 1, wherein an amount of the water to be contacted is not less than 0.1 times by weight that of the zeolite.

3. A pretreatment process according to claim 1, wherein the zeolite is kept in contact with water for from 3 to 1000 hours.

4. A pretreatment process according to claim 1, wherein the zeolite is kept in contact with water at a temperature of 50° to 300° C.

5. A zeolite catalyst obtained by the pretreatment process as defined in claim 1.

6. A process for producing a cyclic alcohol which comprises hydrating a cyclic olefin in the presence of a zeolite catalyst obtained by keeping a zeolite as a catalyst in contact with water.

7. A process according to claim 6, wherein an amount of the water to be contacted is not less than 0.1 times by weight that of the zeolite.

8. A process according to claim 6, wherein the zeolite is kept in contact with water for from 3 to 1000 hours.

9. A process according to claim 6, wherein the zeolite is kept in contact with water at a temperature of 50° to 300° C.

10. A process according to claim 6, wherein the hydration is carried out at a temperature of 20° to 250° C.

11. A process according to claim 6, wherein an amount of water used in the hydration is 1 to 100 moles per mole of the olefin.

12. A process according to claim 6, wherein an amount of the zeolite catalyst used in the hydration is 0.01 to 200 times by weight that of the olefin.

* * * * *